United States Patent [19]

Reiff et al.

[11] 4,115,429

[45] Sep. 19, 1978

[54] LOW-TEMPERATURE STORAGE STABLE LIQUID DIPHENYLMETHANE DIISOCYANATES

[75] Inventors: Helmut F. Reiff; Richard S. Pantone, both of New Martinsville, W. Va.

[73] Assignee: Mobay Chemical Corporation, Pittsburgh, Pa.

[21] Appl. No.: 778,896

[22] Filed: Mar. 18, 1977

[51] Int. Cl.² .......................................... C07C 119/048
[52] U.S. Cl. ...................... 260/453 SP; 260/453 AM; 560/26; 560/27; 528/67; 521/159
[58] Field of Search ................ 260/453 SP, 453 AM; 560/24, 26, 27

[56] References Cited

U.S. PATENT DOCUMENTS

| | | | |
|---|---|---|---|
| 3,362,979 | 1/1968 | Bentley | 260/453 AM |
| 3,394,165 | 7/1968 | McClellan et al. | 260/453 SP |
| 3,644,457 | 2/1972 | Konig et al. | 260/453 SP |
| 3,883,571 | 5/1975 | Allport et al. | 260/453 AM |
| 4,055,548 | 10/1977 | Carleton et al. | 260/77.5 AT |

*Primary Examiner*—Dolph H. Torrence
*Attorney, Agent, or Firm*—Gene Harsh; Joseph C. Gil; R. Brent Olson

[57] ABSTRACT

The instant invention is directed to novel low temperature, storage stable liquid diphenylmethane diisocyanates and to the method of their preparation. The diisocyanates of the instant invention are provided by reacting diphenylmethane diisocyanates having a specified 2,4'-isomer content with polyoxyethylene glycols having molecular weights of from 150 to 1500. It has been surprisingly found that the products of the instant invention are both stable and liquid at −5° C for at least 48 hours. In fact, in many instances, the products of the instant invention show no tendency to crystallize even when stored at −22° C for 100 hours.

18 Claims, No Drawings

LOW-TEMPERATURE STORAGE STABLE LIQUID DIPHENYLMETHANE DIISOCYANATES

BACKGROUND OF THE INVENTION

It is well known that diisocyanates which are liquid at room temperature (i.e., about 25° C) have numerous advantages over solid diisocyanates because they are easier to mix and work with. However, diisocyanates which are liquid at room temperature and which are used on a large technical scale, such as toluene diisocyanate or hexamethylene diisocyanate, are as a rule physiologically harmful due to their high vapor pressure and therefore can only be used if certain safety precautions are taken. For this reason, various attempts have been made, either to start with diisocyanates that are normally liquid at room temperature and to reduce their physiological effects by certain procedures or to start with diisocyanates that are solid at room temperature and to convert these into liquid form. In both cases, however, one usually obtains either isocyanates of higher valency, i.e., tri- or polyisocyanates or higher molecular weight diisocyanates or a combination of these effects.

The most important diisocyanates which are solid at room temperature and which are readily available on a large commercial scale are 4,4'-diphenylmethane diisocyanate and the 2,4'-isomer thereof which melt at 39° C and 34.5° C respectively. Attempts have already been made to liquify both the 4,4'-diphenylmethane diisocyanate and a mixture of the 4,4'-diphenylmethane diisocyanate and a small amount of the 2,4'-isomer. Thus, for example, in U.S. Pat. No. 3,644,457, 1 mol of a diphenylmethane diisocyanate is reacted with from about 0.1 to about 0.3 mols of poly-1,2-propylene ether glycol. While the products made according to this patent have met with commercial success, they still suffer from a serious drawback. Specifically, it has been found that these adducts generally will crystallize anywhere from 5° C to as high as 25° C. In fact, when supplied in commercial quantities, these adducts are generally transported in heated trucks. Additionally, in order to thaw the materials it is generally necessary to heat them to somewhere in excess of 50° to 60° C. While in warmer climates, there may not be any problem, in colder areas where the product may be stored in tanks over a period of time, this tendency to crystallize can become a very serious problem. Similar attempts to form liquid diphenylmethane diisocyanates have been described for example, in U.S. Pat. Nos. 3,384,653 and 3,394,164. The attempts to liquify in both of these instances were based on the addition of, in one case, a trihydrocarbyl phosphate, and, in the other case, small amounts of phosphoric acid. In any event, the storage stability of both of these types of products in again quite good around room temperature, but as the temperature decreases, both types of materials tend to crystallize.

In U.S. application Ser. No. 766,997, filed on Feb. 9, 1977, diisocyanates are described which are both stable and liquid at −5° C for at least 48 hours. The diisocyanates disclosed therein are produced by reacting a diphenylmethane containing at least 15 percent by weight of the 2,4'-isomer with a propylene glycol or poly-1,2-propylene ether glycol. Although such products represent an important advance in the art, the search has continued for other liquid organic diisocyanates.

It is therefore an object of this invention to provide improved liquid organic diisocyanates which are liquid and stable at temperatures lower than room temperature. A further object of this invention is to provide organic diisocyanates which remain liquid even on prolonged storage at low temperatures.

DESCRIPTION OF THE INVENTION

The instant invention is therefore directed to novel diisocyanate compounds which are both stable and liquid at −5° C for at least 48 hours which diisocyanate compounds comprises the reaction product of a diphenylmethane diisocyanate containing at least 20% by weight of the 2,4'-isomer with polyoxyethylene glycol having a molecular weight of from 150 to 1500. The materials are reacted in an NCO/OH ratio of from about 3 : 1 to about 15 : 1, preferably from about 3 : 1 to about 10 : 1 and most preferably from about 3 : 1 to about 6 : 1. It has also been found that many of the novel diisocyanate compounds herein are both stable and liquid at −22° C for 100 hours.

The glycol and the isocyanate can be reacted at temperatures ranging anywhere from room temperature (i.e., about 25°) up to 125° C. Preferably, the reaction temperature is from room temperature to about 90° C and most preferably, from about 40° C to about 80° C.

In general, the diphenylmethane diisocyanates usable according to the instant invention must contain at least 20 percent by weight of the 2,4'-isomer. While theoretically, there is no upper limit to the amount of 2,4'-isomer which could be present in the isocyanate, as a practical matter, due to availability in the present day isocyanate market, it is generally not possible to have the 2,4'-isomer content in excess of 70 percent. Thus, as a practical rule, the diphenylmethane diisocyanates used according to the instant invention will contain from about 20 to about 70 percent by weight of the 2,4'-isomer with the balance being the 4,4'-isomer and 2,2'-isomer and/or various MDI dimers (the 2,2'-isomer and any dimer are generally present only in trace amounts, i.e., less than 1 percent by weight). The lower limit of 20 percent by weight of the 2,4'-isomer is in fact somewhat marginal. In fact, it has been found that at the 20 percent level, some of the reaction products formed are low temperature storage stable while others are not. Preferably, the 2,4'-isomer content is from about 25 to about 65 percent by weight and most preferably from about 40 to about 65 percent by weight.

The liquid diisocyanates which can be prepared according to the instant invention have a relatively low viscosity and can therefore be worked up very easily, e.g., they can be cast or metered through pumps. In addition, they have a very low vapor pressure and are therefore substantially physiologically harmless. Since the reaction can generally be carried out at relatively low temperatures, the diisocyanate structure of the product of the process is completely preserved. Allophanate formation by the reaction of the resulting urethane groups with the isocyanate group to produce a polyisocyanate apparently does not take place to any large degree. This is true even when forming the reaction product at a temperature of 125° C.

The polyoxyethylene glycols usable in the instant invention include essentially any ranging from a molecular weight of 150 (i.e. triethylene glycol) up to molecular weights of about 1500. Specific examples include triethylene glycol, tetraethylene glycols, and various polyoxyethylene glycols.

The process of the instant invention may be carried out by introducing the glycols into the diisocyanate at temperatures of from room temperature up to about 125° C with stirring. Alternatively, the diisocyanate can be introduced into the glycols. The isocyanate content of the products of the process generally amounts to from as low as about 10 percent to as high as about 30 percent.

The products of the process can be used for all types of different polyaddition reactions in the lacquer and plastics industries, e.g. for the production of polyurethane foams or polyurethane elastomers which are in turn useful for the preparation of cushions or gear wheels respectively. Because of their low freezing point, the materials can be transported and stored at reasonably cold temperatures. In fact, it will be clear from the examples which follow, many of the products of the instant invention do not freeze when stored at −22° C for 100 hours. Yet a further advantage of the reaction products of the instant invention resides in the fact that even if the products should freeze, they will readily thaw at room temperature. This is completely different from the materials disclosed in U.S. Pat. No. 3,644,457, which upon freezing, must be heated to in excess of 50° C.

The invention is further illustrated by the following examples in which all parts are by weight unless otherwise specified.

EXAMPLES

EXAMPLES 1 THROUGH 8

In these eight examples, a diphenylmethane diisocyanate (containing 35 percent by weight of the 4,4'-isomer and 65 percent by weight of the 2,4'-isomer) and the various glycols specified in TABLE I were combined under vigorous stirring at 25° C. After a few minutes, the reaction mixtures turned clear and slight exotherm of up to about 50° to 60° C was observed. After the exotherm had leveled off, stirring was continued for an additional 5 hours. Samples were then analyzed for viscosity and NCO content and then stored in a freezer for 48 hours at −5° C. After the 48 hours storage, the samples were removed from the freezer. Results are set forth in TABLE I. The amounts of glycols and isocyanates added were such that the NCO/OH ratio was as specified in the table. Examples 1 and 2 represent comparative examples.

TABLE I

| Example No. | Glycol used | NCO/OH ratio | % NCO by weight calc. | % NCO by weight found | Viscosity cps, 25° C | Storage Stability 48 hours at −5° C |
|---|---|---|---|---|---|---|
| 1 | Ethylene glycol (62.1) | 4.95 | 25.5 | — | phase separation, rock-hard solids | completely solid |
| 2 | Diethylene glycol (106.1) | 4.95 | 24.7 | 24.3 | very high viscosity, gel-type material | gel |
| 3 | Triethylene glycol (150.2) | 4.95 | 23.8 | 23.7 | 685 | liquid |
| 4 | Tetraethylene glycol (194.2) | 4.95 | 22.9 | 22.9 | 795 | liquid |
| 5 | Polyethylene glycol, average MW 297 | 4.95 | 21.7 | 21.5 | 910 | liquid |
| 6 | Polyethylene glycol, average MW 397 | 4.95 | 20.3 | 20.0 | 1100 | liquid |
| 7 | Polyethylene glycol, average MW 600 | 8.0 | 22.6 | 22.2 | 265 | liquid |
| 8 | Polyethylene glycol, average MW 1000 | 8.0 | 19.6 | 19.3 | 455 | liquid |

After bringing the products of Examples 3 through 8 back to room temperature, viscosities and % NCO were rechecked and found to be unchanged.

EXAMPLES 9 THROUGH 13

The process of Examples 1 through 8 were followed except that the isomer distribution was varied as set forth in TABLE II. A constant NCO/OH ratio of 4.95 was used in each instance. The glycol used in each example was tetraethylene glycol. Results are set forth in TABLE II. After bringing the products of Examples 11 through 13 back to room temperature, viscosities and % NCO were rechecked and found to be unchanged.

TABLE II

| Example No. | MDI 4,4'/2,4' Ratio | NCO/OH ratio | % NCO by weight found | Viscosity cps, 25° C | Storage Stability 48 hours at −5° C |
|---|---|---|---|---|---|
| 9 | 100 : 0 | 4.95 | — | rock-hard solids, mp > 80° C | completely solid |
| 10 | 80 : 20 | 4.95 | 22.7 | 685 | completely solid |
| 11 | 60 : 40 | 4.95 | 22.8 | 800 | liquid |
| 12 | 57 : 43 | 4.95 | 22.7 | 685 | liquid |
| 13 | 35 : 65 | 4.95 | 22.9 | 795 | liquid |

EXAMPLES 14 THROUGH 17

The process of Examples 1 through 8 was followed using diphenylmethane diisocyanate containing 65 percent by weight of the 2,4'-isomer and a polyethylene glycol having an average molecular weight of 600. The reaction temperature was 25° C and exotherms were found to be between 35° C and 50° C. After the exotherm had leveled off, stirring was continued for 5 hours. Various NCO/OH ratios were used as specified in TABLE III. Results are set forth in TABLE III. After bringing the products back to room temperature, viscosities and % NCO were rechecked and found to be unchanged.

TABLE III

| Ex. No. | NCO/OH Ratio | % NCO by weight calc. | % NCO by weight found | Viscosity cps, 25° C | Storage Stability 48 hrs. at −5° C |
|---|---|---|---|---|---|
| 14 | 10 | 24.4 | 24.0 | 115 | liquid |
| 15 | 8 | 22.6 | 22.2 | 266 | liquid |
| 16 | 4.9 | 17.9 | 17.2 | 1660 | liquid |
| 17 | 3.0 | 12.4 | 11.7 | 7130 | liquid |

EXAMPLES 18 THROUGH 21

The process of Examples 1 through 8 was followed using an NCO/OH ratio of 3.72, a diphenylmethane diisocyanate containing 65% by weight of the 2,4'-isomer, and triethylene glycol, but using various reaction temperatures, and heated for the times specified in TABLE IV. The temperature, times of reaction and results were as set forth in TABLE IV. % NCO and viscosities remained unchanged after the products were brought back to room temperature.

TABLE IV

| Ex. No. | Reaction Temperature | Reaction Time in hours | % NCO Found | Viscosity + cps, 25° C | Storage Stability 48 hours at −5° C |
|---|---|---|---|---|---|
| 18 | ambient | 8 hrs. | 21.2 | 4000 | liquid |
| 19 | 40° C | 8 hrs. | 21.1 | 4300 | liquid |
| 20 | 65° C | 3 hrs. | 21.1 | 4200 | liquid |
| 21 | 105° C | 1 hr. | 20.7 | 4425 | liquid |

+ All viscosities are measured the day materials were prepared. It was observed that these materials have a thixotropic character.

The products of Examples 2 through 21 were all stored in a deep-freezer for 100 hours at −22° C and checked for stability against freezing and/or crystallization. The results were as set forth in TABLE V.

TABLE V

| Example No. | 100 hrs./−22° C Storage Stability | Comments |
|---|---|---|
| 2 | gel | very high viscosity, gel-like material |
| 3 | liquid | none |
| 4 | liquid | " |
| 5 | liquid | " |
| 6 | liquid | " |
| 7 | complete | material melted to a perfect liquid at ambient temperature without heating, shaking or stirring. |
| | solid | |
| 8 | " | |
| 9 | complete | materials do not melt at ambient temperature; they remain a white crystalline solid. |
| | solid | |
| 10 | " | |
| 11 | liquid | none |
| 12 | " | " |
| 13 | " | " |
| 14 | " | " |
| 15 | " | " |
| 16 | " | " |
| 17 | " | " |
| 18 | " | " |
| 19 | " | " |
| 20 | " | " |
| 21 | " | " |

EXAMPLE 22

To 300 grams of diphenylmethane diisocyanate with a 2,4'-isomer content of 20 percent were added 240 grams of polyethylene glycol (molecular weight of 600) at 50° C under stirring. The temperature of the reaction mixture increased to about 85° C and then dropped within 1 hour to about 55° C. Stirring was continued for 3 hours at 55° C. The NCO/OH ratio used was 3. The percent NCO in the product was found to be 11.8 percent while the viscosity at 25° C was found to be 15,400 cps. The product remained in the liquid state when stored at −5° C for 48 hours and when stored at −22° C for 100 hours. After storage stability was established, no change in either NCO content or viscosity could be determined.

This example serves to illustrate that, as noted earlier, at the 20 percent 2,4'-isomer content level it is certainly possible to produce liquid products within the defined invention (compare Example 10).

EXAMPLES 23 THROUGH 26

The process of Examples 1 through 8 was followed using an NCO/OH ratio of 4.95, a diphenylmethane diisocyanate containing 65 percent by weight of the 2,4'-isomer and triethylene glycol, but using various reaction temperatures and heated for the times specified in TABLE VI. The temperatures, times of reaction and results were as set forth in TABLE VI. Percent NCO and viscosities remained unchanged after the products were brought back to room temperature.

TABLE VI

| Ex. No. | Reaction Temperature | Reaction Time in hours | % NCO Found | Viscosity cps, 25° C | Storage Stability 48 hours at −5° C |
|---|---|---|---|---|---|
| 23 | 25° C | 19 hrs. | 23.9 | 570 | liquid |
| 24 | 40° C | 5 hrs. | 23.9 | 570 | liquid |
| 25 | 65° C | 4 hrs. | 24.2 | 550 | liquid |
| 26 | 105° C | 1 hr. | 23.8 | 605 | liquid |

When stored for 100 hours at −22° C, the products of Examples 23 through 26 remained liquid.

It is to be understood that the foregoing examples are given for the purpose of illustration and that various other materials within the definition of the claims could be used. Although the invention has been described in detail for the purpose of illustration, it is to be understood that such detail is solely for that purpose and that variations can be made therein by those skilled in the art without departing from the spirit and scope of the invention except as it may be limited by the claims.

What is claimed is:

1. A diisocyanate compound which is both stable and liquid at −5° C for at least 48 hours, comprising the reaction product of:
   (a) a diphenylmethane diisocyanate containing at least 20 percent by weight of the 2,4'-isomer, and
   (b) a polyoxyethylene glycol having a molecular weight of from 150 to 1500.

2. The compound of claim 1 wherein said diphenylmethane diisocyanate comprises
   (a) from about 20 to about 70 percent by weight of the 2,4'-isomer, and the balance being
   (b) the 4,4'-isomer.

3. The compound of claim 2, wherein said diphenylmethane diisocyanate comprises:
   (a) from about 25 to about 65 percent by weight of the 2,4'-isomer, and the balance being
   (b) the 4,4'-isomer.

4. The compound of claim 3, wherein said diphenylmethane diisocyanate comprises:
   (a) from about 40 to about 65 percent by weight of the 2,4'-isomer, and the balance being
   (b) the 4,4'-isomer.

5. The compound of claim 2, wherein components (a) and (b) are used in such quantities that the NCO/OH ratio is from about 3 : 1 to about 15:1.

6. The compound of claim 5, wherein said ratio is from about 3:1 to about 10:1.

7. The compound of claim 6, wherein said ratio is from about 3:1 to about 6:1.

8. The compound of claim 1, wherein components (a) and (b) are used in such quantities that the NCO/OH ratio is from about 3:1 to about 15:1.

9. The compound of claim 8, wherein said ratio is from about 3:1 to about 10:1.

10. The compound of claim 9, wherein said diphenylmethane diisocyanate comprises:
(a) from about 25 to about 65 percent by weight of the 2,4'-isomer, and the balance being
(b) the 4,4'-isomer.

11. The compound of claim 9, wherein said ratio is from about 3:1 to about 6:1.

12. The compound of claim 11, wherein said diphenylmethane diisocyanate comprises:
(a) from about 40 to about 65 percent by weight of the 2,4'-isomer, and the balance being
(b) the 4,4'-isomer.

13. A process for the production of diisocyanate compounds which are both stable and liquid at $-5°$ C for at least 48 hours which comprises reacting:
(a) a diphenylmethane diisocyanate containing at least 20 percent by weight of the 2,4'-isomer, and
(b) a polyoxyethylene glycol having a molecular weight of from 150 to 1500.

14. The process of claim 13, wherein said components (a) and (b) are reacted at a temperature of from room temperature to about 125° C.

15. The process of claim 14, wherein said diphenylmethane diisocyanate comprises
(a) from about 20 to about 70 percent by weight of the 2,4'-isomer, and the balance being
(b) the 4,4'-isomer.

16. The process of claim 15, wherein components (a) and (b) are used in such quantities that the NCO/OH ratio is from about 3:1 to about 5:1.

17. The process of claim 16, wherein said components (a) and (b) are reacted at a temperature of from room temperature to about 90° C.

18. The process of claim 17, wherein said components (a) and (b) are reacted at a temperature of from about 40° C to about 80° C.

* * * * *